(12) United States Patent
von Sobbe (10) Patent No.: US 11,029,678 B2
(45) Date of Patent: Jun. 8, 2021

(54) ANALYSIS SYSTEM

(71) Applicant: bnn Holding AG, Weggis (CH)

(72) Inventor: Hans-Ulrich von Sobbe, Diessen a. Ammersee (DE)

(73) Assignee: bnn Holding AG, Weggis (CH)

(*) Notice: Subject to any disclaimer, the term of this patent is extended or adjusted under 35 U.S.C. 154(b) by 361 days.

(21) Appl. No.: 16/300,498

(22) PCT Filed: May 9, 2017

(86) PCT No.: PCT/EP2017/061011
§ 371 (c)(1),
(2) Date: Nov. 9, 2018

(87) PCT Pub. No.: WO2017/194513
PCT Pub. Date: Nov. 16, 2017

(65) Prior Publication Data
US 2019/0227535 A1   Jul. 25, 2019

(30) Foreign Application Priority Data

May 10, 2016 (EP) ..................................... 16168902

(51) Int. Cl.
*G05B 23/02* (2006.01)
*A61B 5/00* (2006.01)
(Continued)

(52) U.S. Cl.
CPC ........ *G05B 23/0254* (2013.01); *A61B 5/0077* (2013.01); *A61B 5/445* (2013.01);
(Continued)

(58) Field of Classification Search
CPC ...... G05B 23/0254; G06N 3/02; G06N 7/023; G06N 3/0436; G06N 7/005; A61B 5/0077;
(Continued)

(56) References Cited

U.S. PATENT DOCUMENTS 7,386,446 B2    6/2008  Schuller et al.
8,903,750 B1 *  12/2014  Bodkin ................. G06N 7/005
                                                  706/14

(Continued)

FOREIGN PATENT DOCUMENTS

CN    1079057 A    12/1993
CN    1295686 A     5/2001
(Continued)

OTHER PUBLICATIONS

Delia-Maria Filimon, et al., Skin Diseases Diagnosis using Artificial Neural Networks, 9th IEEE International Symposium on Applied Computational Intelligence and Informatics, May 15-17, 2014, 189-194, Romania.

(Continued)

*Primary Examiner* — Mohammad K Islam
(74) *Attorney, Agent, or Firm* — Erickson Kernell IP, LLC; Mark C. Young (57) ABSTRACT

A system for controlling an operating condition of an operating system includes a data collector, controller and processing logic comprising a model of the operating system including sets of operation parameters and correlated operating conditions. Values of a portion of the operation parameters are retrieved and form an initial parameter set which is compared with correlated operating conditions. The processing logic determines a correlated operating condition with a corresponding probability of coincidence and for a matching operating condition with the highest probability of coincidence checks whether other matching operating conditions with a similar probability of coincidence exist. If another matching operating condition exists, an additional operation parameter with a similar probability of coincidence is obtained and the process is repeated from the comparison step until no other matching operating conditions with a (Continued)

similar probability of coincidence exist, at which point the matching operating condition is transmitted to the controller.

20 Claims, 3 Drawing Sheets (51) Int. Cl.
*G06K 9/62* (2006.01)
*G06N 3/04* (2006.01)
*G06N 7/00* (2006.01)
*G06N 3/02* (2006.01)
*G06N 7/02* (2006.01)

(52) U.S. Cl.
CPC .......... *A61B 5/7264* (2013.01); *G06K 9/6212* (2013.01); *G06N 3/02* (2013.01); *G06N 3/0436* (2013.01); *G06N 7/005* (2013.01); *G06N 7/023* (2013.01)

(58) Field of Classification Search
CPC .... A61B 5/7264; A61B 5/445; G06K 9/6212; G16H 50/20
See application file for complete search history.

(56) References Cited

U.S. PATENT DOCUMENTS

| | | | |
|---|---|---|---|
| 10,180,339 B1* | 1/2019 | Long | G06N 3/08 |
| 10,599,155 B1* | 3/2020 | Konrardy | B60W 60/0011 |
| 10,821,983 B1* | 11/2020 | Koebler | B60W 10/04 |
| 2004/0078171 A1 | 4/2004 | Wegerich et al. | |
| 2006/0106743 A1* | 5/2006 | Horvitz | G06N 7/005 706/21 |
| 2008/0183444 A1* | 7/2008 | Grichnik | G05B 17/02 703/2 |
| 2008/0194919 A1 | 8/2008 | Farage et al. | |
| 2010/0209881 A1* | 8/2010 | Lin | G09B 19/167 434/65 |
| 2013/0268203 A1 | 10/2013 | Pyloth | |
| 2013/0322711 A1 | 12/2013 | Schultz et al. | |
| 2016/0035150 A1 | 2/2016 | Barfield, Jr. et al. | |
| 2016/0364862 A1 | 12/2016 | Reicher et al. | |

FOREIGN PATENT DOCUMENTS

| | | |
|---|---|---|
| CN | 1914670 A | 2/2007 |
| CN | 101606175 A | 12/2009 |
| CN | 105393252 A | 3/2016 |
| EP | 1064601 B2 | 8/2004 |
| EP | 1873603 A2 | 1/2008 |
| EP | 1921527 A2 | 5/2008 |
| EP | 1921527 A3 | 4/2010 |
| WO | 2007133543 A2 | 11/2007 |
| WO | 2014172671 A1 | 10/2014 |

OTHER PUBLICATIONS

C.B. Crumb Jr., et al, The Automatic Digital Computer as an Aid in Medical Diagnosis, 1959 Proceedings of the Eastern Joint Computer Conference, 1959, 174-180.

* cited by examiner

| | Legend |
|---|---|
| h) | Ascertain at least one parameter |
| i) | Supply parameter to controller |

ANALYSIS SYSTEM

CROSS-REFERENCE TO RELATED APPLICATION

This application claims priority from European patent application No. 16168902.1 filed May 10, 2016, the disclosure of which is hereby incorporated herein in its entirety by reference.

BACKGROUND

The present invention relates to an analysis system for the machine-aided analysis of the operating condition of an operating system. Such an operating system can be for example a sports car during a race. Such racing cars generally travel at the limit of the physical possibilities, for which reason such an operating system in a racing car is constantly connected by radio to an analysis system that continuously evaluates the entire measurement values of different sensors in the racing car and in response to this evaluation the analysis system is able to detect inferior or inferior operating conditions of the racing car and where appropriate to undertake counter-measures, such as for example change the fuel-air composition, change the angle of incline of an aerodynamic wing, change the power curve, change the valve strokes etc. Owing to the fact that data technology is consequently becoming an ever greater portion of the racing event, demands have become more strident to reduce the increasing influence of the data processing systems on the racing event by reducing the amount of data traffic between the racing car and the analysis system at the pit box.

The object of the present invention is to perform an analysis and correct an operating system with respect to inferior operating conditions whilst greatly reducing the volume of data.

SUMMARY

The invention is achieved by means of an analysis system in accordance with claim 1 and by means of a method for analyzing an operating system in accordance with claim 14. Advantageous further developments of the invention are the subject of the attached dependent claims. Preferred embodiments are likewise described in the description and also in the drawing.

As in the case of the known analysis system, the analysis system comprises a data connection to the operating system and/or a data connection to an input device for inputting the values of operation parameters relating to the operating system. It is not necessary for this data connection to be a wired data connection. Particularly in the motor racing sector, data is transmitted between the operating system, in other words the racing car and the analysis system in a wireless manner by radio. The data connection is designed so as to transmit the values of at least two different initial operation parameters relating to the operating system. The analysis system comprises processing logic that comprises in accordance with the invention a model of the operating system. The model is stored in the processing logic and comprises mutual correlations of different operation parameters and normal/inferior/abnormal operating conditions or classes (e.g. operating classes or simply classifications). The analysis system retrieves the values of at least two different initial operation parameters of the operating system but in total only a part of the operation parameters of the operating system that are available via the data connection. Consequently, the analysis system does not evaluate all the operation parameters of the operating system that can be transmitted via the data connection but only a part thereof, as a consequence of which the amount of data that is transmitted between the racing car and the analysis system is significantly reduced. The model comprises a multitude of operation parameters and correlated operating conditions or classes of the operating system and may be embodied as or comprise an associative memory for storing dependencies between different operation parameters of the system and correlated operating conditions and/or classes.

The Inventive Analysis System a) retrieves via the data connection and/or the input device the values of only a part of the operation parameters of the operating system which can be transmitted via the data connection, b) forms an initial parameter set from the values of the retrieved operation parameters and optionally from the value at least of one operation parameter calculated from the retrieved operation parameters, c) compares the initial or an expanded parameter set by means of the model with correlated operating conditions or classes stored in the model, d) determines for the initial or expanded parameter set at least one correlated operating condition or class with a corresponding probability of coincidence, e) determines the operating condition or class with the highest probability of coincidence as matching operating condition or class, f) the processing logic checks whether aside of the matching operating condition or class other matching operating conditions or classes with a similar probability of coincidence exist and/or whether the probability of coincidence of the matching operation condition or class is below a predefined threshold value, g) in the case of the performed check in step f) is positive, the processing logic obtains by means of the model at least one additional operation parameter being correlated with at least one of the operating conditions or classes with similar probability of coincidence, and h) retrieves the value of said additional operation parameter either directly from the operating system or by means of the input device and supplies to step c) an expanded set of operation parameter values, said expanded set comprising the initial or previous parameter set plus said additional operation parameter, i) in the case the performed check in step f) is negative or after an abort criterion has been achieved, the processing logic indicates the at least one operating condition or class with the highest associated probability of coincidence as matching operating condition or class on a display and/or transmits said information to a controller of the operating system.

Thus, the analysis system uses the initially obtained operation parameters and uses the model to check whether this initial set of operation parameters is correlated to a class or operating condition of the operating system. For example in the race car field an excessive temperature of the motor block is correlated to the operating condition or class "overheated condition" which is very dangerous so that immediately counter-steps should be taken.

To analyze abnormal operating conditions the analysis system preferably comprises at least one a reference value memory in which reference values for the values of the (normal) operation parameters of the operating system are stored. If any of these reference values are exceeded by operation parameters (their values) by a threshold value the operating condition can immediately be classified to an abnormal operating condition, whereby by means of the initial operation parameters and the additional operation parameters the problem of the operating system may be effectively classified.

If the system finds several correlated operating conditions or classes belonging to the initial parameter set or the probability of coincidence is below a predefined threshold value then under use of the model additional operation parameters can be requested from the data connection and/or input device to enable the analysis system to specify the correlated operating condition or class with a higher probability of coincidence. Thus, it can not only be ensured that the matching operation condition or class has a much higher probability of coincidence than the next probable operation condition or class, but it can also be ensured via the predefined threshold value that the absolute value of the probability of coincidence lies within a reasonable level. Thus, additional operation parameters are also retrieved if the absolute probability of coincidence is too low, e.g. below 50%. Thus, an adapted predefined threshold value for the probability of coincidence can e.g. be 50%, better 60%, even better 70%. Thus, it can be ensured that the probability of coincidence is high enough to be evaluated as unambiguous result.

Thus, the retrieving of additional parameters is repeated, until the difference between the matching operating condition or class and the next probable operating condition or class is no longer in the area of similarity and if the absolute value of the probability of coincidence is above the predefined threshold value. The area of similarity can be chosen by the skilled person according to the field of application. Similarity normally prevails, if the difference is less than 10%, preferably less than 20% and most preferably less than 30%.

Preferably, the processing logic is designed so as to repeat steps c) to h) until an abort criterion is achieved that relates either to a period of time or to the difference between the probability of coincidence of the most probable operating condition or class and the probability of coincidence of the next-probable operating condition or class, wherein, once the abort criterion has been achieved, in step i) at least two operating conditions with the highest similar probability of coincidence are indicated and/or transmitted to the operating system. Thus, when the abort criterion leads to the termination of the optimization it is quite clear that the difference between the matching operating condition or class and the operating condition or class with the second highest probability of coincidence is not large enough to leave the area of similarity. This means that no unambiguous result is obtained. In this case it is therefore advantageous to indicate the similar best results to enable the skilled person to make a final decision by himself.

Preferably, the processing logic defines a probability of coincidence as similar if the difference between the probability of coincidence of the matching operating condition or class and the probability of the coincidence of a next probable operating condition or class is within a threshold value, for example at most 10%, preferably at most 20%, most preferably at most 30%.

Preferably, the probability of the coincidence is indicated on a display of the analysis system together with the matching operating condition or class as to enable the user to check the probability of the matching result, which enables him to verify the reliability of the result.

Preferably, the processing logic is designed to change the value of operation parameter, which counteracts the classified operating condition or class. Via this feature the analysis system is able to automatically counter-act to an abnormal operating condition.

Preferably, the analysis system is designed to communicate with a controller and/or a data detection device of the operating system. Via this measure, the analysis system may obtain operating parameters directly from the operating system, e.g. via sensors of the operating system. On the other hand, the analysis system can directly control components of the operating system as to counter-act abnormal operating situations.

Preferably, the data connection is connected to an input device of an input terminal and wherein the identity of an additional operation parameter to be input is indicated on a display of the input terminal. In this case the operator knows immediately the operation parameter in questions whose value is to be inputted.

In the inventive analysis system, each operation parameter is indicated with an identity (e.g. name or number) and its correlated value, which may be an analogue or digital value. Thus, each operation parameter can be unambiguously handled in the analysis system.

The processing logic preferably has a decision making network, e.g. a neuronal network. Via this network, not only is a fast processing of the data obtained, but the network has self-learning abilities, so that the accuracy of the results will increase with continuing operation time.

Preferably, the model comprises an associative memory for storing dependencies between different operation parameters of the system and preferably between correlated operating condition or classes.

In this case, the associative memory is preferably self-organized as to be able to include new parameters and to establish dependencies based on the decision making history of the analysis system.

In a preferred embodiment of the invention, the processing logic in connection with the model is configured to calculate the additional operation parameter being of a type which excludes as many competitive operation parameters as possible. It can thus be evaluated which additional operation parameter leads to the exclusion of as many competing operation parameters as possible. This reduces the total number of operation parameters to be considered to obtain the matching operating condition or class. Thus, this feature leads to rapid progress in finding the matching operation condition or class In a preferred embodiment of the invention, a check can be performed in the analysis system by means of the model as to which a change of operation parameters has a positive influence, or in other words counteracts the ascertained inferior operating condition(s). In this case, a control command can be transmitted directly to the operating system and said control command is used to change the corresponding operation parameter of the operating system so as to counteract the inferior operating condition.

In the event that it is established in step f) that multiple (inferior) operating conditions or classes are correlated with the initial set of operation parameters, then at least one additional operation parameter is ascertained by means of the model in steps g) and h), said at least one additional operation parameter being correlated with at least one of the (inferior) operating conditions or classes of similar probability.

The value of the additional operation parameter is retrieved in step h) either directly from the operating system or by way of an input device and subsequently supplied back to method step c) in which the processing logic correlates the values of the operation parameters that are being considered (now expanded by the additional operation parameter) by means of the model with at least one inferior operating condition of the operating system. This loop of the method steps c) to h) is repeated until via the increased number of operation parameter values the model is able to correlate the retrieved operation parameters unambiguously with a correlated single (inferior) operating condition or class. This means that this correlated matching operating condition or class is much more probable than the next-probable operating condition or class. In order to define an unambiguous allocation of said single matching operating condition or class, it is possible to define the similarity of the claim via a maximal difference in the probability of coincidence of the matching operating condition to the next probable operating condition, e.g. being within 10%, 20% or 30% of the matching operating condition value or class value. This means that e.g. if the most probable matching operating condition has a probability of 70% and the next probable has a probability of 48%, an unambiguous allocation is present if the similarity is set to a maximum of 20% difference in the probability. However, this value might differ according to the area of application.

The method steps c) to h) are repeated in an endeavor to improve the analysis system, in particular to provide the model with information. This loop can be repeated until either the difference in the probability of the most probable inferior operating condition and the inferior operating condition with the next-high probability has achieved the limit value or an abort criterion is achieved. The abort criterion can be for example a period of time. It is unacceptable, particularly in the racing car industry that the procedure of determining the inferior operating condition takes a time period of multiple seconds. It is therefore possible to set a time limit of a tenth of a second for calculating the inferior operating condition. Otherwise it is possible to observe a specific consistency of the results in the repeated run-throughs of the steps c) to h). If, for example, it is established that, despite the additional operation parameters that are being considered, the probability of the most probable inferior operating condition hardly changes, the procedure of repeating the steps can be aborted and the most probable inferior operating condition indicated on the display or transmitted to the operating system for further processing, for example so that they can be counteracted by means of influencing a different operation parameter.

Operation parameters that can be transmitted for example from the racing car to the analysis system are for example the engine rotational speed, engine temperature, temperature of engine components such as for example of the turbocharger, optical detection in the region of the exhaust pipe, pressure on the front axle and rear axle, position of air-guiding surfaces such as for example spoilers, parameters of the fuel mixture preparation, charge pressure of the turbo pumps, the signals from accelerometers on the vehicle in order possibly to detect an impaired directional stability of the vehicle. It is possible to influence the operating system by virtue of adjusting parameters in the fuel mixture supply such as for example charge pressure, adjustment of the valve clearances or ventilation opening time periods, adjusting the spoiler position, adjusting the ignition point in time, activating and deactivating the cylinders of the engine, etc. The advantage of the analysis system in accordance with the invention resides in the fact that it is not necessary to constantly transmit the entire range of operation parameters but rather only a small part of perhaps two to ten operation parameters need to be transmitted in comparison to for example 30 possible operation parameters. The analysis system only retrieves additional operation parameters if these are required during the course of detecting an inferior operating or status parameter in the operating system (additional operation parameters) so as to unambiguously determine the inferior operating condition or status.

If, in this case, one of these standard or initial operation parameters exceeds the permissible reference value, this is considered by the analysis system as an inferior operating condition, in response to which the above described analysis algorithm is used, which leads to a corresponding inferior operating condition that is then indicated and can be counteracted possibly by means of adjusting specific operation parameters in the operating system. In the event that it is not possible to unambiguously allocate an inferior operating condition on the basis of the available initial operation parameters because for example with the values of the available operation parameters multiple inferior operating condition could be possible, additional operation parameters are increasingly retrieved, said additional operation parameters being identified by means of the model as correlating to at least one of the possible inferior operating conditions. Consequently, additional operation parameters are only retrieved in special situations, as a consequence of which, the entire volume that is transmitted between the racing car and the analysis system can be significantly reduced. It is preferred that the display not only indicates which inferior operating condition is present but rather that the display also indicates with which probability this inferior operating condition is present so as to provide the operator with an estimation regarding the reliability of the detected inferior operating condition.

The invention does not only allow error situations or abnormal situations to be detected and counteracted but also allows for the detection of inferior or poor operation parameters of the system or even the classification of operating conditions. Thus, additional operation parameters may be retrieved form the input device until the unambiguous classification of the operating condition is possible.

It is preferred that the processing logic of the analysis system is designed so as to change the value at least of one operating system-related operation parameter, which counteracts the ascertained inferior operating condition. In this manner, the analysis system is not only able to detect an inferior operating condition of the operating system but rather it can also counteract this inferior operating condition so as to ensure that the operating system can still run.

In one advantageous embodiment of the invention, the model and/or decision making network of the processing logic is embodied as a neural network that, on the basis of the analytic activity of the analysis system, automatically creates correlations between the operation parameters and/or between operation parameters and inferior operating condition of the operating system. The processing logic is therefore designed so as to feed into the model correlations of values of the operation parameters and inferior operating conditions, said correlations being ascertained during the course of the analysis procedure. In other words, the model has a self-learning function and is therefore able to continuously improve the correlations, which are available there, between operation parameters and between inferior operating conditions. The obtained analysis results are therefore constantly improving as the use of the system increases. Suitable embodiments for the model are for example a fuzzy logic or a genetic algorithm or neuronal network so as to improve the logic links of the neural network a decision making network.

It is preferred that the data connection is designed in such a manner so as to ensure bi-directional data transmission between the controller and/or a data acquisition device of the operating system. It is possible in this manner not only to retrieve all retrievable operation parameters from the operating system but rather the controller can also be prompted to change the operation parameters of the operating system so as to counteract an inferior operating condition that has been detected in the analysis system.

In one advantageous further development of the invention, the data input channel is connected to an input device of an input terminal, wherein a required additional operation parameter is indicated on a display of the input terminal as a variable to be input. In this manner, an operator is informed which operation parameter of the operating system the analysis system still requires in order to deliver an improved statement regarding an inferior operating condition of the operating system. In this case, interactivity between the operating system and the analysis system are improved by involving the operator.

The invention likewise relates to a method for the machine-aided analysis of the operation parameter of an operating system. In accordance with the invention, only a part of the operating system-related operation parameters that can be transmitted via the data connection are retrieved for monitoring the operating condition of the operating system, according to which each of the steps c) to h) already mentioned above are performed based on the reduced number of operation parameters possible by retrieving additional operation parameters to define an inferior operating condition of the operating system and to indicate this inferior operating condition or to influence the operating system so as to counteract the inferior operating condition. The advantages and details of this method have already been described above in connection with the analysis system in accordance with the invention.

It is to be noted that the method for monitoring very different operating systems can be used such as for example racing cars, production machines, building technology, said method can even be used to aid diagnostic procedures in the medical field. The above described preferred embodiments of the invention can be combined with one another in any manner.

Preferably, the process logic comprises a decision making network, e.g. a neuronal network, as well as an associative memory for dependencies between different status parameters of the system. This associative memory is advantageously self-organized so as to be able to include new parameters and to establish dependencies based on decision making history. The process logic further comprises a signal output device in which the "best decision" of the decision making network is outputted in the form of the requested system parameter or parameter set. The signal output device may be connected to a screen to display the output parameters or the change of the output parameters. The parameters may alternatively or additionally also be directly connected to device drivers of the operating system in question, e.g. in the above mentioned embodiment regarding the Formula 1 area to a valve control or turbo-loader control, spoiler angle control, gasoline feed control, air feed control of the combustion engine and/or chassis of the race car.

Preferably, the processing logic comprises a sensor input in the form of a data connection or input device mentioned in claim 1. Via this sensor input the system receives status and feedback data from status sensors mounted in the operating system or from persons feeding this data via the input device, e.g. a keyboard. This is a kind of feed-back information which provides the process logic with feedback information about how the change of outputted parameters affect the status of the operating system. This newly found correlation can also be fed to the associative memory in form of new associations between system status and the new operation parameters. Thus, the whole system is via the feed-back loop self-controlling and self-learning to automatically learn all correlations and dependencies between the change of operation parameters according to the operating history of the analysis system and the effect on status information read by the sensor input in response to these parameter changes.

Preferably, an initial parameter set is verified by identifying contradictory information, by using step g) and h) to obtain a additional operation parameter of said parameter set. It can, for example, be that one sensor is mal-functioning. In this case, one operation parameter always deviates from the parameter sets corresponding with a defined operating condition or class. If the additional operation parameter also matches the other correct parameters or even is contradicting the wrong parameter value, the detector can be indicated as faulty and the "correct" parameter set without the faulty parameter value can be considered.

The operating system may also be a database, in which case with the present invention it is better possible to classify subjects or objects of the database in a certain data class. The subjects/objects are then characterized by subject-/object parameters. The subject-/object parameters thus correspond to the operation parameters of the invention and the aim is to retrieve additional object/subject parameters if it is not possible to unambiguously classify a subject/object to a certain class of the database.

Thus, a possible further embodiment of the invention refers to dating agencies. Currently, a wide variety of parameters of persons (subjects) to be handled have to be fed to a dating agency database and processing system. Usually the processing system of a dating agency handles a lot of parameters to characterize a person and to evaluate which persons might fit together. Unfortunately, this list of parameters is really long, which is uncomfortable for the users.

With the present invention, the number of parameters to be input by the users can be essentially reduced. Thus, via the model correlations between parameters can be evaluated as to exclude several other parameters which would according to the model not cope with the parameters already inputted. Furthermore, via the model, the processing logic is able to evaluate which additional parameter would lead to the exclusion of most competitive parameters and thus leads to a quicker solution of a dating matching problem. Thus, the persons in the database can effectively and unambiguously be classified as to match certain criteria.

A further field of application is the work of a job agency. Also here, different parameters are linked to the job seeking persons, which is necessary to classify them according to certain job classes on the market. A table of the parameters of a job agency is shown hereinafter.

| No. | Question | worker | courier | plumber | builder | banker |
|---|---|---|---|---|---|---|
| 1 | school education | | | | | |
| | 1 Secondary schools | 0.8 | 0.8 | 0.4 | 0.8 | 0.1 |
| | 2 Qualified Degree | 0.5 | 0.5 | 0.8 | 0.4 | 0.1 |

-continued

| No. | Question | worker | courier | plumber | builder | banker |
|---|---|---|---|---|---|---|
| | 3 middle school | 0.5 | 0.5 | 0.9 | 0.2 | 0.5 |
| | higher school | 0.5 | 0.5 | 0.3 | 0.1 | 0.8 |
| | high school with examination | 0.5 | 0.5 | 0.2 | 0.1 | 0.9 |
| 2 | Which qualification? | | | | | |
| | none | 0.8 | 0.5 | 0.2 | 0.9 | 0.0 |
| | assistant/journeyman | 0.4 | 0.7 | 0.7 | 04 | 0.4 |
| | 2 Master | 0.2 | 0.5 | 0.8 | 0.4 | 0.4 |
| | 3 Bachelor FH | 0.0 | 0.3 | 0.4 | 0.2 | 0.7 |
| | 4 Bachelor Univ | 0.0 | 0.2 | 0.3 | 0.0 | 0.7 |
| | 5 Master | 0.0 | 0.1 | 0.2 | 0.0 | 0.9 |
| 3 | Age? | | | | | |
| | <20 | 0.5 | 0.1 | 0.1 | 0.5 | 0.5 |
| | 20-30 | 0.5 | 0.9 | 0.5 | 0.5 | 0.5 |
| | 30-40 | 0.5 | 0.8 | 0.5 | 0.5 | 0.5 |
| | 40-50 | 0.5 | 0.5 | 0.5 | 0.5 | 0.5 |
| | >50 | 0.5 | 0.1 | 0.2 | 0.5 | 0.5 |
| 4 | Base Language Knowledge | | | | | |
| | 1 Native | 0.5 | 0.8 | 0.9 | 0.5 | 0.9 |
| | 2 learned | 0.5 | 0.7 | 0.8 | 0.5 | 0.7 |
| | 3 basic knowledges | 0.5 | 0.1 | 0.1 | 0.5 | 0.0 |
| 5 | working experience | | | | | |
| | less than one year | 0.5 | 0.5 | 0.2 | 0.3 | 0.1 |
| | 1 to 5 years | 0.5 | 0.5 | 0.5 | 0.5 | 0.4 |
| | 5 to 10 years | 0.5 | 0.5 | 0.7 | 0.6 | 0.7 |
| | more than 10 years | 0.5 | 0.5 | 0.8 | 0.3 | 0.9 |
| 6 | hobbies | | | | | |
| | 1 climbing | 0.5 | 0.5 | 0.5 | 0.5 | 0.1 |
| | 2 diving | 0.5 | 0.5 | 0.5 | 0.5 | 0.1 |
| | 3 skiiing | 0.5 | 0.5 | 0.5 | 0.5 | 0.5 |
| | 4 walking | 0.5 | 0.5 | 0.5 | 0.5 | 0.8 |
| | 5 sailing | 0.5 | 0.5 | 0.5 | 0.5 | 0.7 |

The values in the table are probability values which are used by a processing logic having a fuzzy logic. Of course, this table is not complete. There are numerous additional parameters to be evaluated, as e.g. driver license, software knowledge, current or past working field, etc.

Another example for the application of the invention is the configuration of cars or computer networks. The operation parameters of the invention here are configuration parameters. During the configuration of cars or computer networks there is a variety of mutually exclusive parameters to be considered. The analysis system preferably tries to get in the beginning of the analyzing process a further configuration parameter from the input device which leads to the exclusion of as many competitive parameters as possible. Thus, the whole configuration process can be simplified and shortened.

Particularly in configuration tasks, there are a lot of mutually excluding parameters. The inventive system is able to tailor the retrieving or requesting of parameters from the users by asking for parameters which exclude as many other competitive parameters as possible. It has further to be considered that there are parameter groups which coexist independently, as. e.g. type of motor, outer appearance and inner appearance, although there also might be correlations between them (a certain appearance is only possible with a certain type of motor etc.).

In the configuration of computer networks, there is a multitude of configuration parameters to consider which include the processing performance, the access and output of data from the network, the system architecture, the main software application, the estimated number of users, the price and maintenance of hardware components, the lifetime of hardware components, the cooling requirement etc.

Another field of application is the health management e.g. in a company, where a certain business type of the company has a large influence on the type of health risk management. Parameters for health management are type of business, number of employees, ratio male/female, e.g. for each department separately, e.g. for the manufacture department, sales department, administration department, management department: department/corresponding operating field, employee data and health risk evaluation.

A further field of application of the invention can be building monitoring. The management of large buildings involves a variety of monitored operation parameters as temperature, humidity, movement of the building (in high skyscrapers), elevator status, traffic flow, sunshine intensity and—direction, energy consumption, noise emission. These parameters can be used to regulate control of air conditioning, elevator group control, traffic flow guide, operation of generators etc. The problems are similar to the above mentioned race car problem, where the monitoring may face a prohibited or poor or inferior status condition and then tries to analyze the complete building condition to look for countermeasures by changing other operation parameters to counteract the prohibited or inferior status (e.g. temperature).

The reference value can of course be a reference value range.

Following terms are used as synonyms: condition—state—status; value—value range; coincidence—existence; correlation—interdependency; inferior—abnormal; optimizing—error detection;

It should be understood that the inventive system comprises soft- and hardware components having the above mentioned combined functionality and that the inventive method describes the functionality which can be performed by the inventive system. Thus, features from the inventive system may be employed for the inventive method and vice versa.

BRIEF DESCRIPTION OF THE DRAWINGS

The invention is described herein by way of example with reference to an exemplary embodiment in conjunction with the schematic drawing, in which.

DETAILED DESCRIPTION

Figure 1:
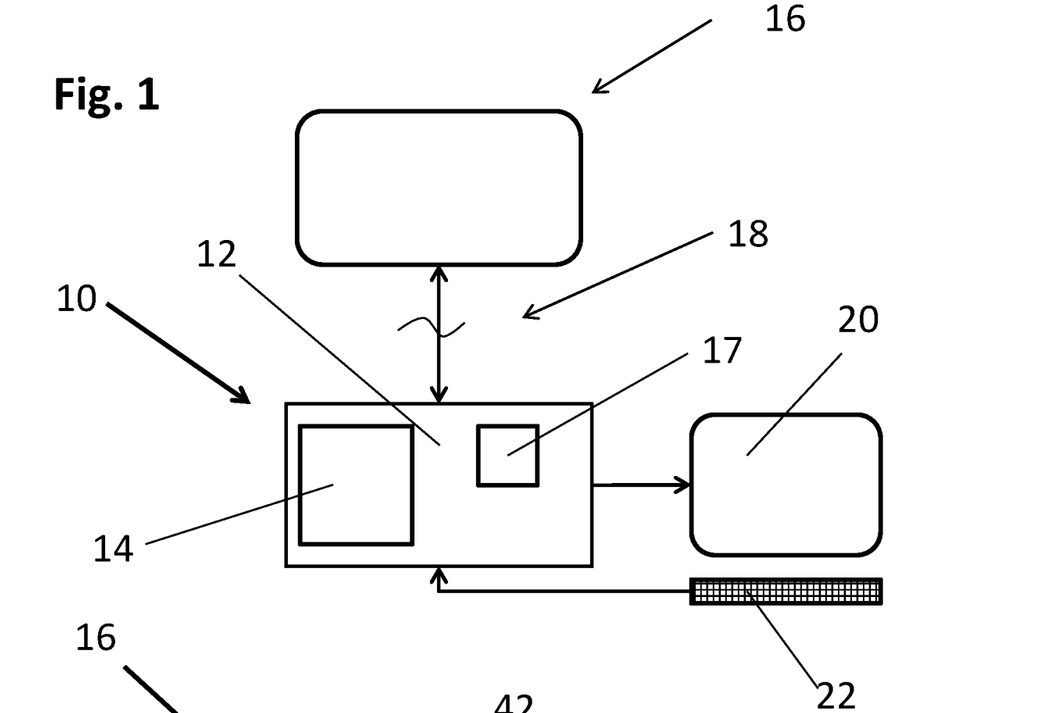
FIG. 1 illustrates a view of the components of an analysis system in accordance with the invention in a wireless connection to an operating system, for example a racing car.

FIG. 1 illustrates an analysis system 10 comprising processing logic 12 for example a microprocessor in which a model 14 of an operating system 16 is embodied, wherein the analysis system 10 communicates with the operating system 16, for example a racing car, via a wireless, bi-directional radio connection 18. The processing unit 12 further comprises, in addition to the model 14, a reference value memory 17 in which the reference values of all possible operation parameters of the operating system 16 are stored. The analysis system 10 further comprises a display 20 and an input keyboard 22 for displaying or inputting values. The analysis system 10 is embodied so as to monitor or to analyze the activity of the operating system 16 by retrieving only a portion of its operation parameters that can be transmitted via the data connection 18 and to report the inferior operating condition or to counteract against said inferior operating condition.

Figure 2:
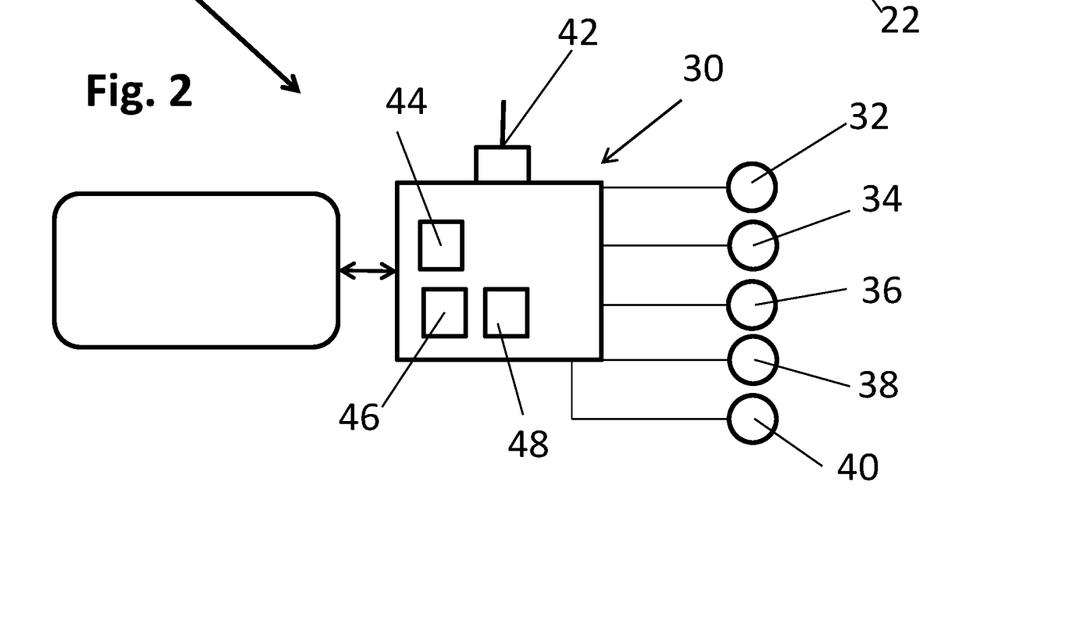
FIG. 2 illustrates a detailed view of the operating system for explaining the inputted and transmitted operation parameters.

The operating system 16 is described in FIG. 2 by way of example with reference to a racing car. Said racing car comprises a controller 30 that is connected to different sensors, for example a tire pressure sensor 32, engine temperature sensor 34, rpm counter 36, axle pressure sensor 38, spoiler position sensor 40. A portion of these values are transmitted by the controller 30 by way of a radio transmitter 42 on demand or regularly to the analysis system 10. Active operation parameters such as for example the injection pressure 44, ignition points in time 46 or the spoiler position 48 can be changed via the radio connection 42. In this manner, the analysis system 10 can influence the operating system 16 in an active manner by means of the controller 30 so as to counteract against a detected inferior operating condition.

Figure 3:
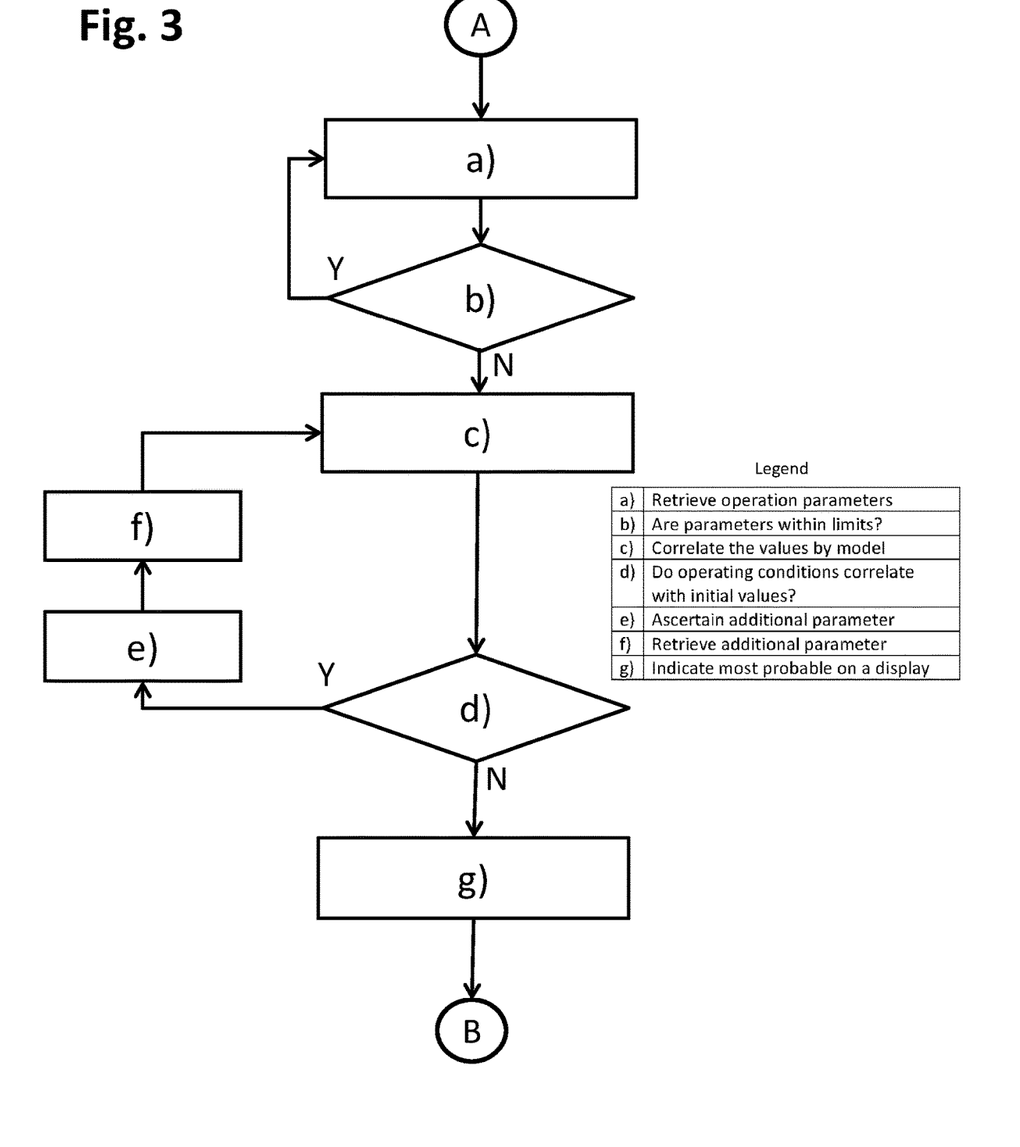
FIG. 3 illustrates a flow chart relating to the procedure of analyzing inferior operating conditions of the operating system.

The method sequence for analyzing the operating system 16 is illustrated in FIG. 3. The procedure starts at Point A, and in step a) of the procedure, the values of at least two operation parameters of the operating system 16, but only a portion of the operating system-related operation parameters that are retrieved via the data connection, are retrieved. A check is performed in the procedural step b) as to whether the retrieved operation parameters are within the limits of a reference value that is stored in the reference value memory 17. If this is the case, the procedure returns to step a). If the reference value is exceeded by at least one of the retrieved operation parameters or by the calculated operation parameters, then the procedure continues to step c) in which the processing logic 12 of the analysis system 10 correlates the values of the initial set of operation parameters by means of the model 14 with at least one inferior or abnormal operating condition of the operating system 16. Thereafter it is checked in step d) whether several inferior operating condition with similar probabilities are correlated with the initial set of operation parameter values. If this is not the case, the procedure continues to step g) in which the most probable inferior operating condition with the associated probability is indicated on a display and/or is transmitted to a controller of the operating system. The procedure can subsequently continue so as to regulate or control the operating system in accordance with FIG. 4.

In the event that it is established in step d) that multiple inferior operating conditions with similar probability are correlated with the operation parameter values of the parameter set, the processing logic 12 ascertains by means of the model 14 at least one additional operation parameter that is correlated with at least one of the inferior operating conditions of similar probability of coincidence. This is done so as to be able to better define the inferior operating condition by means of the additional operation parameter. Subsequently, in step f), the additional operation parameter is retrieved either directly from the operating system via the data connection 18 or by way of the input device 22 in conjunction with the display 20, as a consequence of which a set of operation parameter values is obtained, said set being expanded by the additional operation parameter. This is now supplied back to step c). It should now be possible by means of the additional operation parameter to provide a result with an improved probability of coincidence with respect to the actual prevailing inferior operating condition. In the event that this should not yet be the case, in step d) the procedure branches again into the steps c) to f) in which then additional operation parameters are retrieved from the operating system or inputted by way of the input device until finally the inferior operating condition has been ascertained with sufficient accuracy or an abort criterion is achieved that includes for example a specific period of time, for example 0.1 s, or a sufficiently small change in the probability value of the most probably inferior operating condition with each additional passage.

Figure 4:
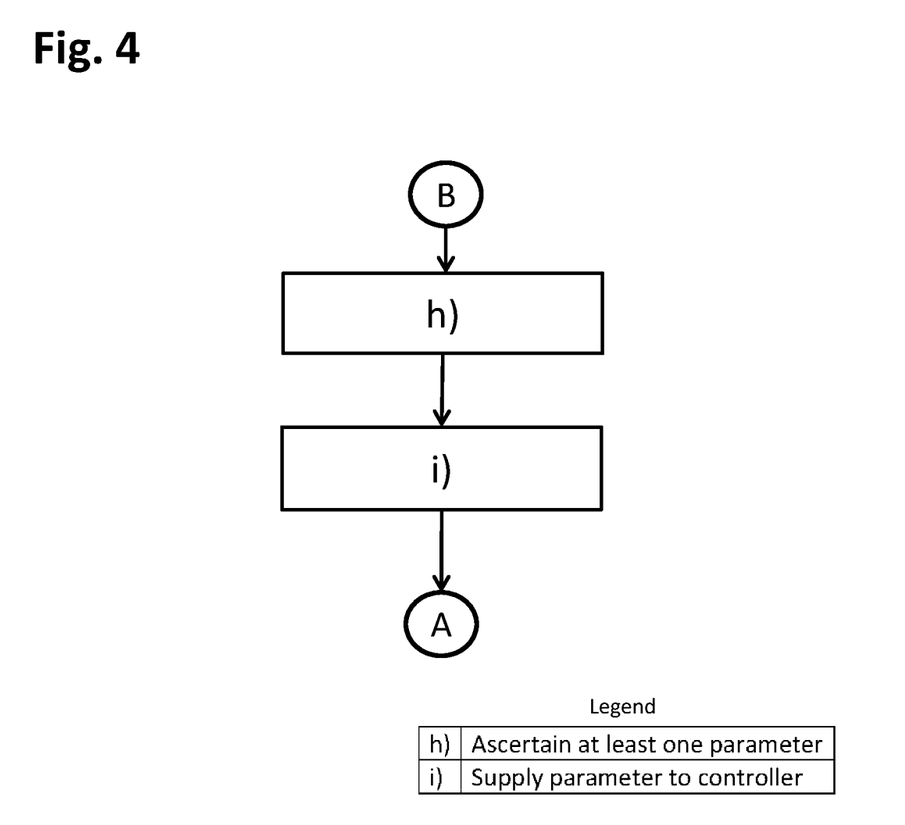
FIG. 4 illustrates a flow diagram of a control method for influencing the operating system after performing the analysis method in accordance with FIG. 3, said flow diagram placing the control procedure at the end of the analysis procedure in accordance with FIG. 3.

After performing the analysis procedure in accordance with FIG. 3, it is possible in accordance with FIG. 4, which commences at the end B of the analysis procedure in accordance with FIG. 3, by means of the model 14 to ascertain at least one operation parameter that is counteracting the ascertained inferior operating condition, said operation parameter to counteract the inferior operating condition. This at least one counteracting operation parameter value is then supplied in step i) to the controller 30 of the operating system 16 so as to perform the corresponding control in order to counteract the inferior operating condition. In addition, or as an alternative thereto, these changed operation parameter values can be indicated by way of the display 20 to the operator as a control action that is to be performed in order to manually redress the inferior operating condition. It is possible for example to provide that prior to transmitting the counteracting operation parameter so as to control the operating system the operator must first give authorization by way of the input device 22.

The invention is not limited to the described exemplary embodiment but rather can be varied within the protective scope of the attached claims.

What is claimed is:

1. An analysis system for machine-aided analysis of an operating condition of a vehicle operating system, comprising:
 a data connection to the vehicle operating system and/or to an input device for retrieving/inputting values of operation parameters of the vehicle operating system, said data connection designed for transmitting the values of operation parameters of the vehicle operating system to a processing logic of an analysis system, which processing logic comprises a model of the vehicle operating system, which model comprises sets of operation parameters and correlated operating conditions or classes of the vehicle operating system, said analysis system configured to:
 a) retrieve via the data connection and/or the input device the values of only a part of the operation parameters of the vehicle operating system which can be transmitted via the data connection,
 b) form an initial parameter set from the values of the retrieved operation parameters or from the value at least of one operation parameter calculated from the retrieved operation parameters,
 c) compare the initial or an expanded parameter set by means of the model with correlated operating conditions or classes stored in the model,
 d) determine for the initial or expanded parameter set at least one correlated operating condition or class with a corresponding probability of coincidence,
 e) determine the operating condition or class with a highest associated probability of coincidence as a matching operating condition or class,
 f) check by the processing logic, whether it is true that, aside from the matching operating condition or class, other matching operating conditions or classes with a similar probability of coincidence exist and/or whether the probability of coincidence of the matching operation condition or class is below a predefined threshold value, g) obtain, if the check in step f) true, by the processing logic by means of the model at least one further operation parameter being correlated with at least one of the operating conditions or classes with similar probability of coincidence, and h) retrieve the value of said further operation parameter either directly from the vehicle operating system or by means of the input device and supplies to step c) an expanded set of operation parameter values, said expanded set comprising the initial or previous parameter set plus said further operation parameter, i) indicate on a display and/or transmit to a controller of the vehicle operating system, by the processing logic, if the check in step f) is not true or after an abort criterion has been achieved, the at least one operating condition or class with the highest associated probability of coincidence as the matching operating condition or class.

2. The analysis system as claimed in claim 1, wherein the processing logic is designed to repeat steps c) to h) until the abort criterion is achieved that relates either to a period of time or to the difference between the probability of coincidence of the most probable operating condition or class and the probability of coincidence of the next-probable operating condition or class, wherein, once the abort criterion has been achieved, in step i) at least two operating conditions with a highest similar probability of coincidence are indicated and/or transmitted to the vehicle operating system.

3. The analysis system as claimed in claim 1, wherein the processing logic defines a probability of coincidence as similar if the difference between the probability of coincidence of the matching operating condition or class and the probability of the coincidence of a next probable operating condition or class is less than or equal to 30%.

4. The analysis system as claimed in claim 1, wherein the probability of the coincidence is indicated on a display of the analysis system together with the matching operating condition or class.

5. The analysis system as claimed in claim 1, wherein the processing logic is designed to change the value of at least one operation parameter which counteracts the matching operating condition or class.

6. The analysis system as claimed in claim 1, wherein the model comprises a fuzzy logic.

7. The analysis system as claimed in claim 1, wherein the data connection is designed to communicate with a controller and/or a data detection device of the vehicle operating system.

8. The analysis system as claimed in claim 1, wherein the data connection is connected to an input device of an input terminal and wherein the identity of an additional operation parameter to be input is indicated on a display of the input terminal.

9. The analysis system as claimed in claim 1, wherein the processing logic has a neural network decision making network.

10. The analysis system as claimed in claim 1, wherein the model comprises an associative memory for dependencies between different operation parameters of the system.

11. The analysis system as claimed in claim 10, wherein the associative memory is self-organized such that the associative memory includes new parameters and establishes dependencies based on decision making history.

12. The analysis system as claimed in claim 1, wherein the processing logic in connection with the model is configured to calculate the further operation parameter being of a type which excludes competitive operation parameters.

13. The analysis system as claimed in claim 1, wherein said analysis system further comprises a reference value memory in which reference values for the values of the operation parameters relating to different operating conditions or classes of the vehicle operating system are stored.

14. A method for machine-aided analysis of a condition of a vehicle operating system, wherein a model of the vehicle operating system is used, having a processing logic, on the basis of a neural network, which model correlates different operation parameters with correlated operating conditions or classes of the vehicle operating system, wherein a data connection is provided for retrieving/changing operation parameters of the vehicle operating system, the method comprising:

a) retrieving, via the data connection and/or the input device, the values of only a part of the operation parameters of the vehicle operating system which can be transmitted via the data connection;

b) forming, from the values of the retrieved operation parameters and/or from the value of at least one operation parameter calculated from the retrieved operation parameters, an initial parameter set;

c) comparing, by means of the model, the initial or an expanded parameter set with correlated operating conditions or classes stored in the model;

d) calculating, for the initial or expanded parameter set, at least one correlated operating condition or class with a corresponding probability of coincidence;

e) calculating, as a matching operating condition or class, the operating condition or class with a highest associated probability of coincidence;

f) checking whether it is true that, aside from the matching operating condition or class, other matching operating conditions or classes with a similar probability of coincidence exist and/or whether the probability of coincidence of the matching operation condition or class is below a predefined threshold value;

g) obtaining, by the processing logic by means of the model, if the performed check in step f) is true at least one further operation parameter being correlated with at least one of the operating conditions or classes with similar probability of coincidence, and;

h) retrieving the value of said further operation parameter either directly from the vehicle operating system or by means of the input device and supplying to step c) an expanded set of operation parameter values, said expanded set comprising the initial or previous parameter set plus said further operation parameter; and i) indicating on a display and/or transmitting to a controller of the vehicle operating system, by the processing logic, if the performed check f) is not true or after an abort criterion has been achieved, the at least one operating condition or class with the highest associated probability of coincidence as the matching operating condition or class.

15. The method as claimed in claim 14, wherein steps c) to h) are repeated until an abort criterion is achieved that relates either to a period of time or to the difference between the probability of coincidence of the most probable operating condition or class and the probability of coincidence of the next-probable operating condition or class, wherein, once the abort criterion has been achieved, in step i) at least the two operating conditions with a highest similar probability of coincidence are indicated and/or transmitted to the vehicle operating system.

16. The method as claimed in claim 14, wherein probabilities of coincidence are defined as similar if the difference between the probability of coincidence of the matching operating condition or class and the probability of the coincidence of a next probable operating condition or class less than or equal to 30%.

17. The method as claimed in claim 14, wherein correlations of values of the operation parameters and inferior operating conditions are fed into the model, said correlations being ascertained during the analysis procedure.

18. The method as claimed in claim 14, wherein an initial parameter set is verified by identifying contradictory information, by using step g) and h) to obtain a further operation parameter of said parameter set.

19. An analysis and control system for analyzing and controlling an operating condition of a vehicle operating system, the analysis and control system comprising a controller and a data detection device associated with the vehicle operating system and a data connection, the data connection communicating between the data detection device and a processor running a processing logic and communicating between the processor and the controller of the vehicle operating system, the data detection device detecting and transmitting, through the data connection, values of the operation parameters of the vehicle operating system to the processor for use by the processing logic, which processing logic comprises a model of the vehicle operating system with sets of operation parameters and correlated operating conditions of the vehicle operating system, the analysis and control system configured to:
  a) retrieve, via the data connection, the values of only a portion of the operation parameters of the vehicle operating system which can be transmitted via the data connection;
  b) form an initial parameter set from the values of the retrieved operation parameters or from an expanded parameter set from the initial parameter set and the value of at least of one operation parameter calculated from the retrieved operation parameters;
  c) compare the initial or an expanded parameter set by means of the model with correlated operating conditions stored in the model;
  d) determine for the initial or expanded parameter set at least one correlated operating condition with a corresponding probability of coincidence;
  e) determine a matching operating condition comprising the operating condition with a highest associated probability of coincidence as a matching operating condition;
  f) check, by the processing logic whether it is true that, aside from the matching operating condition, other matching operating conditions with a similar probability of coincidence exist and whether the probability of coincidence of the matching operation condition is below a predefined threshold value;
  g) obtain, if the result of the check in step f) is true, by the processing logic, using the model, at least one additional operation parameter being correlated with at least one of the operating conditions with a similar probability of coincidence, and retrieves the value of said additional operation parameter from the vehicle operating system and supplies to step c) an expanded set of operation parameter values, said expanded set of operation parameter values comprising the initial or previous parameter set plus said additional operation parameter; and
  i) display on a display and transmit to a controller of the vehicle operating system, by the processing logic, if the result of the check in step f) is not true or after an abort criterion has been achieved, the at least one operating condition with the highest associated probability of coincidence as the matching operating condition.

20. A method for machine-aided analysis of a condition of a vehicle operating system having a controller and data detection device associated therewith and using a processing logic comprising a neural network and including a model of the vehicle operating system, which model correlates different operation parameters with correlated operating conditions of the vehicle operating system, and a data connection is provided for retrieving or changing operation parameters of the vehicle operating system, wherein the method includes the steps of:
  a) retrieving, via the data connection, the values of only a portion of the operation parameters of the vehicle operating system which can be transmitted via the data connection;
  b) forming an initial parameter set from the values of the retrieved operation parameters or from an expanded parameter set from the initial parameter set and the value of at least of one operation parameter calculated from the retrieved operation parameters;
  c) comparing the initial or an expanded parameter set by means of the model with correlated operating conditions stored in the model;
  d) determining for the initial or expanded parameter set at least one correlated operating condition with a corresponding probability of coincidence;
  e) determining a matching operating condition comprising the operating condition with a highest associated probability of coincidence;
  f) checking, via the processing logic, whether it is true that, aside from the matching operating condition, other matching operating conditions with a similar probability of coincidence exist and whether the probability of coincidence of the matching operation condition is below a predefined threshold value;
  g) if the result of the check in step f) is, true obtaining via the processing logic using the model at least one additional operation parameter correlated with at least one of the operating conditions with a similar probability of coincidence, and retrieving the value of said additional operation parameter from the vehicle operating system and supplying to step c) an expanded set of operation parameter values, said expanded set of operation parameter values comprising the initial or previous parameter set plus said additional operation parameter; and
  i) if the result of the check in step f) is not true or after an abort criterion has been achieved, displaying the matching operating condition comprising the at least one operating condition with the highest associated probability of coincidence and transmitting said information to the controller of the vehicle operating system.

* * * * *